United States Patent [19]

Nakanishi et al.

[11] Patent Number: 5,620,944
[45] Date of Patent: Apr. 15, 1997

[54] PHENYLIMIDAZOLE DERIVATIVES, HERBICIDES COMPRISING SAID DERIVATIVES, AND USAGES OF SAID HERBICIDES

[75] Inventors: Hiroyuki Nakanishi, Ibaraki; Masanori Yoshida, Hashimoto; Takashi Ootsuka, Kawachinagano; Hideo Kanno, Ibaraki, all of Japan

[73] Assignee: Nihon Nohyaku Co., Ltd., Tokyo, Japan

[21] Appl. No.: 543,065

[22] Filed: Oct. 13, 1995

Related U.S. Application Data

[63] Continuation of Ser. No. 125,205, Sep. 23, 1993, abandoned.

[30] Foreign Application Priority Data

Sep. 26, 1992 [JP] Japan ................................. 4-281021

[51] Int. Cl.$^6$ ..................... A01N 43/50; C07D 233/68; C07D 233/64
[52] U.S. Cl. ..................... 504/275; 504/219; 504/248; 540/603; 546/210; 548/314.7; 548/338.1; 548/341.5; 548/342.5; 548/343.1; 548/343.5
[58] Field of Search ..................... 504/219, 248, 504/275; 540/603; 546/210; 548/314.7, 338.1, 341.5, 342.5, 343.1, 343.5

[56] References Cited

U.S. PATENT DOCUMENTS 4,369,186   1/1983   Beck et al. ..................... 548/343.1
4,666,932   5/1987   Cereda et al. ..................... 514/400

FOREIGN PATENT DOCUMENTS

| 52-111573 | 9/1977 | Japan . |
| 56-92874 | 7/1981 | Japan . |
| 2-262560 | 10/1990 | Japan . |
| 56150070 | 10/1990 | Japan . |
| WO93/15074 | 8/1993 | WIPO . |

OTHER PUBLICATIONS

Ellis et al, "Antifungal activity of some, etc" J. Pharm. Pharmacol., 1964, 16, 400–407.

*Primary Examiner*—Patricia L. Morris
*Attorney, Agent, or Firm*—Cushman Darby & Cushman IP Group of Pillsbury Madison & Sutro LLP

[57] ABSTRACT

The present invention discloses phenylimidazole derivatives having herbicidal activities, represented by general formula (I)

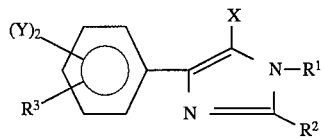

($R^1$ and $R^2$ each represent an alkyl group or the like; $R^3$ represents an alkoxy group or the like; X is a hydrogen atom or a halogen atom; and two Ys each represent a halogen atom); processes for producing said derivatives; herbicidal compositions each comprising said derivative as an active ingredient; and a method for weed control, using said herbicidal composition.

12 Claims, No Drawings

PHENYLIMIDAZOLE DERIVATIVES, HERBICIDES COMPRISING SAID DERIVATIVES, AND USAGES OF SAID HERBICIDES

This is a continuation of application Ser. No. 08/125,205, filed on Sep. 23, 1993 now abandoned.

BACKGROUND OF THE INVENTION

1. Field of the Invention

The present invention relates to a phenylimidazole derivative represented by the following general formula (I)

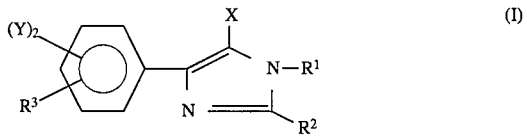

wherein $R^1$ is a hydrogen atom, an alkyl group of 1–10 carbon atoms, a haloalkyl group of 1–5 carbon atoms, an alkenyl group of 3–5 carbon atoms or an alkynyl group of 3–5 carbon atoms; $R^2$ is a hydrogen atom, an alkyl group of 1–5 carbon atoms or a haloalkyl group of 1–5 carbon atoms; X is a hydrogen atom or a halogen atom; two Ys, which may be the same or different, are each a halogen atom; and $R^3$ is a group represented by the following general formula

{A' is O, S or NH; and $R^4$ is a hydrogen atom, an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, a group represented by the following general formula

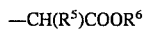

($R^5$ is a hydrogen atom or an alkyl group of 1–5 carbon atoms; and $R^6$ is a hydrogen atom, an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, an alkoxyalkyl group of 2–6 total carbon atoms or an alkoxyalkoxyalkyl group of 3–9 total carbon atoms), or a group represented by the following general formula

($R^5$ is the same as defined above; and $R^7$ and $R^8$, which may be the same or different, are each a hydrogen atom or an alkyl group of 1–6 carbon atoms but may together form an alkylene group of 4–6 carbon atoms)}, or a group represented by the following general formula

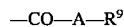

{A is O or S; and $R^9$ is a hydrogen atom, an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, a group represented by the following general formula

($R^5$ and A are the same as defined above; and $R^{10}$ is a hydrogen atom, an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, an alkoxyalkyl group of 2–6 total carbon atoms or an alkoxyalkoxyalkyl group of 3–9 total carbon atoms), or a group represented by the following general formula

($R^5$, $R^7$ and $R^8$ are the same as defined above)}; processes for production of said derivatives; herbicides comprising said derivatives; and methods for controlling weeds using said herbicides.

2. Related Art

Japanese Patent Application Kokai (Laid-Open) No. 262560/1990 discloses imidazole compounds represented by the following general formula, as intermediate compounds for producing pest-controlling agents for use in agriculture and horticulture, fungicides for use in medicines, or herbicides.

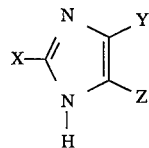

The above imidazole compounds differ from the phenylimidazole derivatives of the present invention because the Y in the above general formula is a hydrogen atom, a chlorine atom or a bromine atom.

SUMMARY OF THE INVENTION

The present inventors made an extensive study to develop a novel herbicide and, as a result, found that the phenylimidazole derivatives represented by the above general formula (I) are novel compounds unreported in any literature and have excellent herbicidal activities at low application dosages. The finding has led to the completion of the present invention.

DETAILED DESCRIPTION OF THE INVENTION

The phenylimidazole derivatives of the general formula (I) according to the present invention have tautomers as shown below when the $R^1$ in the general formula (I) is a hydrogen atom. The present invention includes such tautomers.

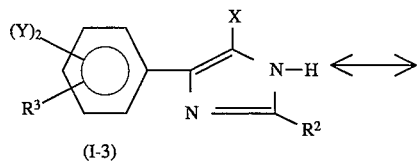

(I-3)

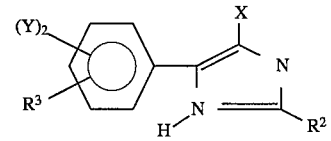

In the above, $R^2$, $R^3$, X and two Ys are the same as defined above.

Of the substituents in the present phenylimidazole derivatives of the general formula (I), preferable as $R^1$ are haloalkyl groups wherein the halo portion is one or more halogen atoms which may be the same or different, such as chloromethyl, dichloromethyl, trichloromethyl, chlorofluoromethyl, fluoromethyl, difluoromethyl, trifluoromethyl, chloroethyl, dichloroethyl, trichloroethyl, fluoroethyl, difluoroethyl, trifluoroethyl, tetrafluoroethyl, chlorodifluoroethyl, dichlorodifluoroethyl, chloropropyl, dichloropropyl, fluoropropyl, difluoropropyl, trifluoropropyl, tetrafluoropropyl, pentafluoropropyl, chlorobutyl, dichlorobutyl, fluorobutyl, difluorobutyl and the like. Particularly preferable as $R^1$ is a difluoromethyl group and a tetrafluoroethyl group.

Preferable as $R^2$ are alkyl groups such as methyl, ethyl, n-propyl, isopropyl, n-butyl, isobutyl, sec-butyl, tert-butyl, n-pentyl and the like; and haloalkyl groups such as chloromethyl, dichloromethyl and the like.

Preferable as $R^3$ are alkoxy groups such as methoxy, ethoxy, n-propoxy, isopropoxy, n-butoxy, isobutoxy, sec-butoxy, tert-butoxy, n-pentyloxy and the like; haloalkoxy groups such as difluoromethoxy, trifluoromethoxy and the like; alkenyloxy groups such as propenyloxy, butenyloxy and the like; alkynyloxy groups such as propynyloxy, butynyloxy and the like; cycloalkyloxy groups such as cyclopropyloxy, cyclopentyloxy, cyclcohexyloxy and the like; alkoxycarbonylalkoxy groups such as methoxycarbonylmethoxy, ethoxycarbonylmethoxy, n-propoxycarbonylmethoxy, isopropoxycarbonylmethoxy, n-butoxycarbonylmethoxy, methoxycarbonylethoxy, ethoxycarbonylethoxy, n-propoxycarbonylethoxy, isopropoxycarbonylethoxy, n-butoxycarbonylethoxy and the like; haloalkoxycarbonylalkoxy groups such as chloromethoxycarbonylmethoxy, chloroethoxycarbonylmethoxy, chloropropoxycarbonylmethoxy, chloromethoxycarbonylethoxy, chloroethoxycarbonylethoxy, chloropropoxycarbonylethoxy and the like; cycloalkyloxycarbonylalkoxy groups such as cyclopropyloxycarbonylmethoxy, cyclopentylcarbonylmethoxy, cyclohexylcarbonylmethoxy and the like; alkoxyalkoxycarbonylalkoxy groups such as methoxymethoxycarbonylmethoxy, methoxyethoxycarbonylmethoxy, ethoxyethoxycarbonylmethoxy and the like; alkoxyalkoxyalkoxycarbonylalkoxy groups such as methoxymethoxymethoxycarbonylmethoxy, methoxyethoxyethoxycarbonylmethoxy, ethoxyethoxyethoxycarbonylmethoxy, methoxymethoxymethoxycarbonylethoxy, methoxyethoxyethoxycarbonylethoxy, ethoxyethoxyethoxycarbonylethoxy and the like; alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl and the like; alkoxycarbonylalkoxycarbonyl groups such as methoxycarbonylmethoxycarbonyl, ethoxycarbonylmethoxycarbonyl, n-propoxycarbonylmethoxycarbonyl, methoxycarbonylethoxycarbonyl, ethoxycarbonylethoxycarbonyl, n-propoxycarbonylethoxycarbonyl and the like; alkoxyalkoxycarbonylalkoxycarbonyl groups such as methoxymethoxycarbonylmethoxycarbonyl, methoxyethoxycarbonylmethoxycarbonyl, ethoxyethoxycarbonylmethoxycarbonyl, ethoxyethoxycarbonylethoxycarbonyl and the like; alkoxyalkoxyalkoxycarbonylalkoxycarbonyl groups such as methoxymethoxymethoxycarbonylmethoxycarbonyl, methoxyethoxyethoxycarbonylmethoxycarbonyl, ethoxyethoxyethoxycarbonylmethoxycarbonyl, methoxymethoxymethoxycarbonylethoxycarbonyl, methoxyethoxyethoxycarbonylethoxycarbonyl, ethoxyethoxyethoxycarbonylethoxycarbonyl and the like; and so forth.

Preferable as X are halogen atoms such as chlorine atom, bromine atom and the like.

Preferable as each Y are a chlorine atom and a fluorine atom.

The present phenylimidazole derivatives represented by the general formula (I) can be produced, for example, by the following processes with the respective reaction paths being shown schematically.

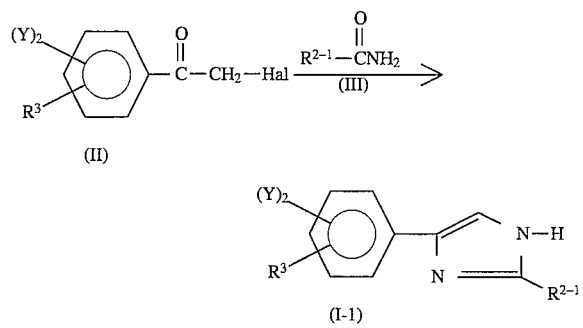

In the above, $R^{2-1}$ is a hydrogen atom or an alkyl group of 1–5 carbon atoms; $R^3$ and two Ys are the same as defined above; and Hal is a halogen atom.

In the present reaction, a compound represented by the general formula (II) is reacted with a compound represented by the general formula (III) in the presence or absence of an inert solvent, whereby a compound represented by the general formula (I-1) can be produced.

This reaction can be conducted according to the procedure described in Chem. Ber., 86, 88 (1935), Tetrahedron Lett., 1967, 265, etc.

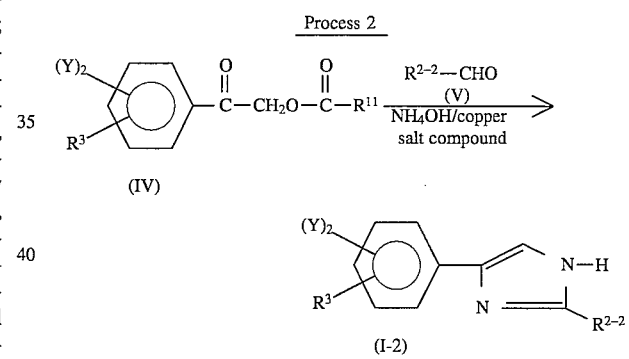

In the above, $R^{2-2}$ and $R^{11}$ are an alkyl gorup of 1–5 carbon atoms; and $R^3$ and two Ys are the same as defined above.

In the present reaction, a compound represented by the general formula (IV) is reacted with an aldehyde represented by the general formula (V) in the presence of ammonia water and a copper salt compound (e.g. copper acetate), whereby a phenylimidazole derivative represented by the general formula (I-2) can be produced.

This reaction can be conducted according to the procedure described in J. Org. Chem., 1983, 48, 3745, etc.

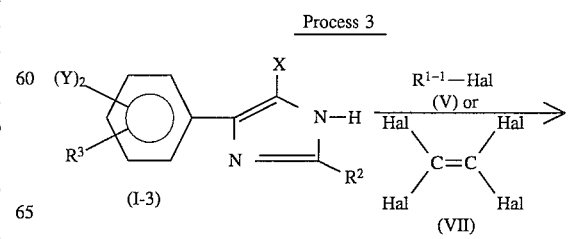

Process 3

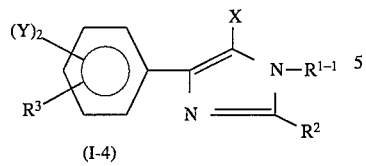

(I-4)

In the above, $R^{1-1}$ is an alkyl group of 1–10 carbon atoms, a haloalkyl group of 1–5 carbon atoms, an alkenyl group of 3–5 carbon atoms or an alkynyl group of 3–5 carbon atoms, $R^2$, $R^3$, X, two Ys and Hal are the same as defined above.

In the present reaction, a phenylimidazole derivative represented by the general formula (I-3) is reacted with a halide represented by the general formula (VI) or (VII) in the presence of a base in the presence or absence of an inert solvent, whereby a phenylimidazole derivative represented by the general formula (I-4) can be produced.

The inert solvent usable in the present reaction can be any inert solvent as long as it does not significantly hinder the progress of the reaction. It can be exemplified by aromatic hydrocarbons such as benzene, toluene, xylene and the like; alcohols such as methanol, ethanol, propanol, glycol and the like; ethers such as diethyl ether, tetrahydrofuran, dioxane and the like; ketones such as acetone, methyl ethyl ketone, cyclohexanone and the like; esters such as ethyl acetate and the like; amides such as dimethylformamide, dimethylacetamide and the like; dimethyl sulfoxide; and water. These inert solvents can be used alone or in admixture.

The temperature of the present reaction can be selected from the range of room temperature to the boling point of the inert solvent used and is preferably in the range of 40°–140° C.

The base usable in the present reaction is an inorganic base or an organic base. The inorganic base includes, for example, sodium carbonate, sodium hydride, sodium hydrogencarbonate, potassium carbonate, sodium hydroxide and potassium hydroxide. The organic base includes, for example, alcoholates of alkali metals, trimethylamine, triethylamine, pyridine, diethylaniline and 1,8-diazabicyclo-[5,4,0]-7-undecene.

When the reaction is conducted in an organic solvent and an aqueous solvent, it is possible to use a phase transfer catalyst such as tetra-n-butylammonium bromide, triethylbenzylammonium chloride or the like.

The amount of the base used can be appropriately selected from the range of one to more moles per mole of the phenylimidazole derivative represented by the general formula (I-3). It is preferably in the range of 2 to 10 moles. It can be 0.01–1 mole per mole of said derivative when a phase transfer catalyst is used.

Since the present reaction is an equimolar reaction, the reactants are used in equimolar amounts. However, any reactant may be used in excess.

The reaction time is appropriately selected from the range of several minutes to 48 hours.

After the completion of the reaction, the reaction mixture is subjected to separation of product by an ordinary method and as necessary further to purification of product, whereby an intended product can be isolated.

Process 4

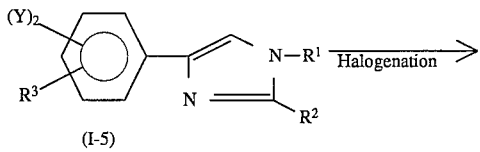

(I-5)

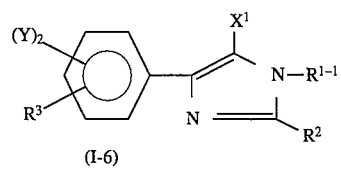

(I-6)

In the above, $X^1$ is a halogen atom, $R^1$, $R^2$, $R^3$ and two Ys are the same as defined above.

In the present reaction, a phenylimidazole derivative represented by the general formula (I-5) is halogenated with a halogenating agent in the presence of an inert solvent, whereby a phenylimidazole derivative represented by the general formula (I-6) can be produced.

The inert solvent usable in the present reaction can be any inert solvent as long as it does not significantly hinder the progress of the reaction. It can be exemplified by halogenated hydrocarbons such as methylene chloride, chloroform, carbon tetrachloride and the like; aromatic hydrocarbons such as benzene, toluene, xylene and the like; esters such as ethyl acetate and the like; nitriles such as acetonitrile, benzonitrile and the like; acyclic ethers such as methyl cellosolve diethyl ether and the like; cyclic ethers such as dioxane, tetrahydrofuran and the like; sulfolane; dimethylformamide; dimethylsulfone; dimethyl sulfoxide; water; phosphorus oxychloride; and glacial acetic acid. These inert solvents can be used alone or in admixture.

The halogenating agent used in the present reaction includes, for example, chlorine, phosphorus trichloride, phosphorus pentachloride, phosphorus oxychloride, sulfuryl chloride, N-chlorosuccinimide (NCS), bromine and N-bromosuccinimide (NBS).

The amount of the halogenating agent used can be appropriately selected from the range of 0.5 mole to excess moles per mole of the phenylimidazole derivative represented by the general formula (I-5).

The reaction temperature can be appropriately selected from the range of 0° C. to the boiling point of the inert solvent used. It is preferably in the range of 10° C. to 50° C.

The reaction time varies depending upon the scale and temperature of the reaction, but can be appropriately selected from the range of several minutes to 48 hours.

After the completion of the reaction, the reaction mixture containing an intended product is subjected to an operation such as solvent extraction or the like by an ordinary method and as necessary further to purification by recrystallization or column chromatography, whereby a phenylimidazole derivative represented by the general formula (I-6) can be produced.

Process 5

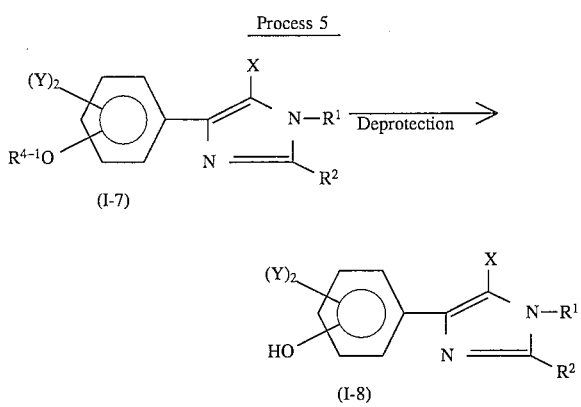

In the above, $R^1$, $R^2$, X and two Ys are the same as defined above, and $R^{4-1}$ is an alkyl group of 1–5 carbon atoms.

In the present reaction, a phenylimidazole derivative represented by the general formula (I-7) is hydrolyzed with a mineral acid, a halogen, a Lewis acid or the like in the presence or absence of an inert solvent, whereby a phenylimidazole derivative represented by the general formula (I-8) can be produced.

The present reaction can be conducted according to the procedure described in J. Am. Chem. Soc., 73, 5765 (1951), etc.

Process 6

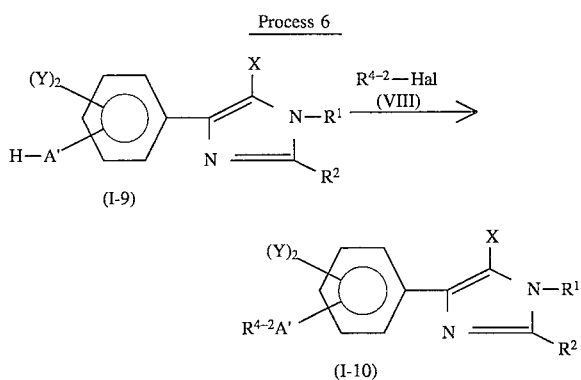

In the above, $R^1$, $R^2$, X, two Ys, A' and Hal are the same as defined above; and $R^{4-2}$ is an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms or a group represented by the following general formula

—CH($R^5$)COO$R^6$ wherein $R^5$ is a hydrogen atom or an alkyl group of 1–5 carbon atoms, and $R^6$ is a hydrogen atom, an alkyl group of 1–10 carbon atoms, a haloakyl group of 1–5 carbon atoms, an alkenyl group of 3–5 carbon atoms, an alkynyl group of 3–5 carbon atoms, a cycloalkyl group of 3–6 carbon atoms, an alkoxyalkyl group of 2–6 total carbon atoms or an alkoxyalkoxyalkyl group of 3–9 total carbon atoms.

In the present reaction, a phenylimidazole derivative represented by the general formula (I-9) is reacted with a halide represented by the general formula (VIII) in the presence of a base in the presence or absence of an inert solvent, whereby a phenylimidazole derivative represented by the general formula (I-10) can be produced.

The inert solvent usable in the present reaction can be any inert solvent as long as it does not significantly hinder the progress of the reaction. It can be exemplified by halogenated hydrocarbons such as methylene chloride, chloroform, carbon tetrachloride and the like; aromatic hydrocarbons such as benzene, toluene, xylene and the like; esters such as ethyl acetate and the like; nitriles such as acetonitrile, benzonitrile and the like; acyclic ethers such as methyl cellosolve diethyl ether and the like; cyclic ethers such as dioxane, tetrahydrofuran and the like; sulfolane; dimethylformamide; dimethylsulfone; dimethyl sulfoxide; and water. These inert solvents can be used alone or in admixture.

When a mixed solvent consisting of water and an organic solvent is used, a phase transfer catalyst such as triethylbenzylammonium chloride or the like may be used together with a base.

The base usable in the present reaction is an inorganic base or an organic base. The inorganic base includes, for example, hydroxides, carbonates or alcoholates of alkali metals or alkaline earth metals such as sodium, potassium, magnesium, calcium and the like. The organic base includes, for example, triethylamine and pyridine.

Since the present reaction is an equimolar reaction, the phenylimidazole derivative represented by the general formula (I-9) and the halide represented by the general formula (VIII) are used in equimolar amounts. However, either of them may be used in excess.

The reaction temperature can be appropriately selected from the range of 0° C. to the boiling point of the inert solvent used, but is preferably in the range of 10° C. to the boling point of the inert solvent used.

The reaction time varies depending upon the scale and temperature of the reaction but can be appropriately selected from the range of several minutes to 48 hours.

After the completion of the reaction, the reaction mixture containing an intended product is subjected to an operation such as solvent extraction or the like by an ordinary method and as necessary further to purification by recrystallization or column chromatography, whereby the intended product can be produced.

Process 7

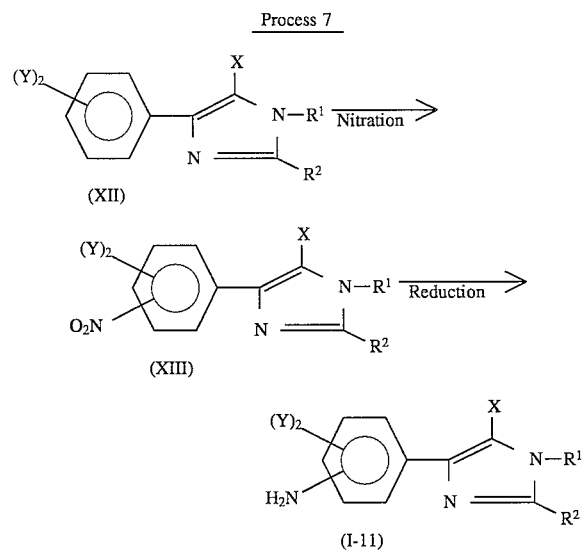

In the above, $R^1$, $R^2$, X and two Ys are the same as defined above.

In the present reaction, a compound represented by the general formula (XII) is nitrated in the presence of an inert solvent to obtain a compound represented by the general formula (XIII), and the compound (XIII) is reduced in the presence of an inert solvent, whereby a phenylimidazole derivative represented by the general formula (I-11) can be produced.

7-1. Nitration

The nitrating agent usable in the nitration can be exemplified by (a) a mixture of concentrated nitric acid or fuming nitric acid and concentrated sulfuric acid and (b) acetyl nitrate formed by mixing concentrated nitric acid and acetic anhydride.

The inert solvent usable in the nitration is a mineral acid such as sulfuric acid, hydrochloric acid or the like.

Since the present reaction is an equimolar reaction, the nitrating agent is used in an amount equimolar to the compound represented by the general formula (XII), but may be used in excess.

The reaction temperature can be appropriately selected from the range of −10° C. to 140° C.

The reaction time depends upon the scale, temperature, etc. of the reaction but is appropriately selected from the range of several minutes to 48 hours.

After the completion of the reaction, the reaction mixture containing an intended product is poured into ice water and the resulting crystals are collected by filtration, or the resulting aqueous mixture is subjected to solvent extraction or the like to isolate the intended product; the crystals or the isolated product is purified as necessary; thereby, the intended product can be produced.

7-2. Reduction

The inert solvent usable in the reduction can be any inert solvent as long as it does not significantly hinder the progress of the reaction. It can be exemplified by alcohols such as methanol, ethanol, propanol and the like; ethers such as diethyl ether, methyl cellosolve, dioxane, tetrahydrofuran and the like; organic acids such as acetic acid and the like; mineral acids such as hydrochloric acid and the like; and water.

The reducing agent used in the reduction can be exemplified by zinc, iron, tin and tin chloride when the reduction is conducted under an acidic condition. A zinc powder can be used even under a basic condition.

When the reduction is conducted by a catalytic hydrogenation method, it can be conducted at normal pressure or under pressure. In this case, there can be used, for example, Raney nickel, palladium carbon, palladium oxide, platinum, platinum black, platinum on sulfide carbon and rhodium-alumina.

The amount of the reducing agent used is equimolar to excess and is generally excess when the reduction is conducted under an acidic condition.

When the reduction is conducted by a catalytic hydrogenation method, the amount of the catalyst used is 2–20% by weight based on the weight of the compound represented by the general formula (XIII) when Raney nickel or the like is used, and 0.02–5% by weight when a noble metal catalyst such as platinum, palladium or the like is used.

The reaction temperature is appropriately selected from the range of 0° C. to 150° C.

The reaction time depends upon the scale, temperature, etc. of the reaction but is appropriately selected from the range of several minutes to 48 hours.

After the completion of the reaction, when the reduction has been conducted under an acidic condition, the reaction mixture containing an intended product is poured into ice water and is subjected to solvent extraction or the like under a basic condition to isolate the intended product; or when the reduction has been conducted by a catalytic hydrogenation method, the reaction mixture is filtered for catalyst removal and the filtrate is concentrated to obtain the intended product. The product is purified as necessary by column chromatography or the like, whereby the intended product can be produced.

Process 8

(XII) → Chlorosulfonylation →

(XIV) → Reduction →

(I-12)

In the above, $R^1$, $R^2$, X and two Ys are the same as defined above.

In the present reaction, a compound represented by the general formula (XII) is subjected to chlorosulfonylation in the presence of an inert solvent and the compound (XII) is reduced in the presence of an inert solvent, whereby a phenylimidazole derivative represented by the general formula (I-12) can be produced.

8-1. Chlorosulfonylation

The inert solvent usable in the chlorosulfonylation can be exemplified by halogenated hydrocarbons such as methylene chloride, chloroform, carbon tetrachloride and the like; nitriles such as acetonitrile and the like; ethers such as methyl cellosolve, dioxane, tetrahydrofuran and the like; and mineral acids such as concentrated sulfuric acid and the like.

The chlorosulfonylation can be conducted by the use of chlorosulfonic acid or the like. It can also be conducted by a process which comprises conducting sulfonation with fuming sulfuric acid, converting the resulting sulfonic acid into an alkali metal salt, and chlorinating the alkali metal salt with phosphorus pentachloride to obtain an intended chlorosulfonation product, or by a process which comprises allowing fuming sulfuric acid to act and then allowing carbon tetrachloride to act to obtain an intended chlorosulfonation product.

The amount of the chlorosulfonic acid used can be appropriately selected from the range of an equimolar amount to an excess molar amount, but is preferably an excess molar amount.

The amount of fuming sulfuric acid or carbon tetrachloride used can be appropriately selected from the range of an equimolar amount to an excess molar amount.

The reaction temperature is appropriately selected from the range of 0° C. to 180° C.

The reaction time depends uon the scale, temperature, etc. of the reaction but is appropriately selected from the range of several minutes to 48 hours.

After the completion of the reaction, the reaction mixture containing an intended product is poured into water; the resulting mixture is subjected to solvent extraction or the like to isolate the intended product; as necessary, the product is purified by column chromatography or the like; thereby, the intended product can be produced.

8-2. Reduction

The reduction is conducted in the presence of an inert solvent such as glacial acetic acid or the like. As the reducing agent, there can be used, for example, zinc, tin and tin chloride. The amount of the reducing agent used is appropriately selected from the range of an equimolar amount to an excess molar amount.

The reaction temperature is appropriately selected from the range of 0° C. to 180° C.

The reaction time depends upon the scale, temperature, etc. of the reaction but is appropriately selected from the range of several minutes to 48 hours.

After the completion of the reaction, the reaction mixture containing an intended product is poured into water; the resulting mixture is subjected to solvent extraction or the like to isolate the intended product; as necessary, the product is purified by column chromatography or the like; thereby, the intended product can be produced.

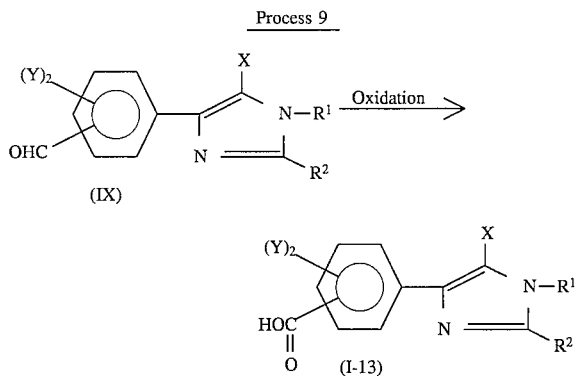

In the above, $R^1$, $R^2$, X and two Ys are the same as defined above.

In the present reaction, an imidazole represented by the general formula (IX) is oxidized with an oxidizing agent in the presence of an inert solvent, whereby a phenylimidazole derivative represented by the general formula (I-13) can be produced.

The inert solvent usable in the present reaction includes aromatic hydrocarbons such as benzene, toluene, xylene and the like; pyridine; water; etc. These inert solvents can be used alone or in admixture.

The oxidizing agent usable in the present reaction includes oxidants such as potassium permanganate, potassium bichromate and the like. The amount of the oxidizing agent used is appropriately selected from the range of 1 to 5 moles per mole of the imidazole represented by the general formula (IX) and is preferably in the range of 4–5 moles.

The reaction temperature is appropriately selected from the range of 0° C. to the boiling point of the inert solvent used, but is preferably in the range of 30° C. to 180° C.

The reaction time depends upon the scale and temperature of the reaction but is appropriately selected from the range of several minutes to 48 hours.

After the completion of the reaction, the reaction mixture containing an intended product is subjected to an operation such as solvent extraction or the like by an ordinary method; the obtained product is purified as necessary by recrystallization or column chromatography; thereby, the intended product can be produced.

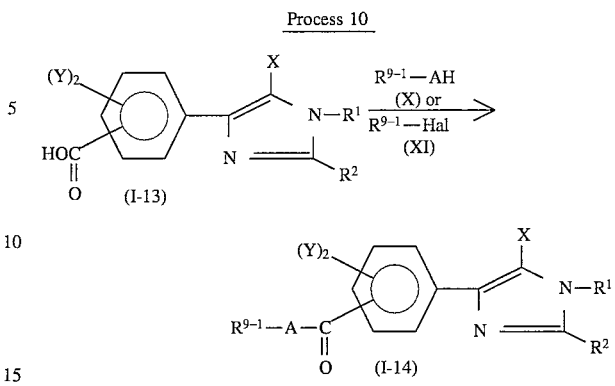

In the above, $R^1$, $R^2$, A, X, two Ys and Hal are the same as defined above; and $R^{9-1}$ is an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, a group represented by the following general formula $$—CH(R^5)CO—A—R^{10}$$

($R^5$ and A are the same as defined above, and $R^{10}$ is a hydrogen atom, an alkyl group of 1–10 carbon atoms, a haloalkyl group of 1–5 carbon atoms, an alkenyl group of 3–5 carbon atoms, an alkynyl group of 3–5 carbon atoms, a cycloalkyl group of 3–6 carbon atoms, an alkoxyalkyl group of 2–6 total carbon atoms or an alkoxyalkoxyalkyl group of 3–9 total carbon atoms) or a group represented by the following general formula $$—CH(R^5)CON(R^7)R^8$$

($R^5$, $R^7$ and $R^8$ are the same as defined above).

In the present reaction, a phenylimidazole derivative represented by the general formula ((I-13) is reacted with a compound represented by the general formula (X) or a compound represented by the general formula (XI) in the presence or absence of a base or a catalyst in the presence or absence of an inert solvent, whereby a phenylimidazole derivative represented by the general formula (I-14) can be produced.

When an catalyst is used in the present reaction, the catalyst includes mineral acids such as sulfuric acid, hydrochloric acid and the like; organic acids such as p-toluenesulfonic acid and the like; Lewis acids such as boron fluoride etherate and the like; dicyclohexylcarbodiimide (DCC); etc.

The present reaction is conducted according to a procedure similar to that used in Process 6, whereby an intended product can be produced.

After the completion of the reaction, the reaction mixture containing an intended product is subjected to an operation such as solvent extraction or the like by an ordinary method; the obtained product is purified as necessary by recrystallization or column chromatography; thereby, the intended product can be produced.

Process 11

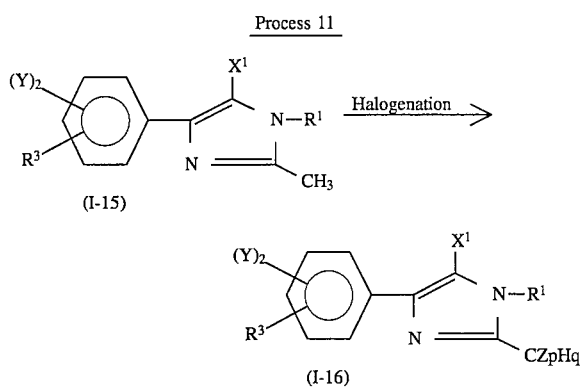

In the above, $R^1$, $R^3$, $X^1$ and two Ys are the same as defined above; Z is a halogen atom other than a fluorine atom; p is an integer of 1–3; and q is an integer of 0–2.

In the present reaction, a phenylimidazole derivative represented by the general formula (I-15) is halogenated (not fluorinated) in the presence or absence of an inert solvent, whereby a phenylimidazole derivative represented by the general formula (I-16) can be produced.

The present reaction is conducted according to a procedure similar to that used in Process 4, whereby an intended product can be produced.

In Table 1 are shown typical compounds of the present phenylimidazole derivative represented by the general formula (I). However, the present derivative is not restricted to these compounds.

TABLE 1

General formula (I')

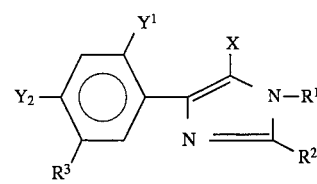

| No. | $R^1$ | $R^2$ | X | $Y^1$ | $Y^2$ | $R^3$ | Properties |
|---|---|---|---|---|---|---|---|
| 1 | H | $CH_3$ | H | F | Cl | $OCH_3$ | m.p. 205.0–207.0° C. |
| 2 | H | H | H | F | Cl | $OC_3H_7$-i | m.p. 152.0–153.0° C. |
| 3 | H | $CH_3$ | H | F | Cl | $OC_3H_7$-i | m.p. 183.0–185.5° C. |
| 4 | $CH_3$ | $CH_3$ | Cl | F | Cl | $OCH_3$ | m.p. 112.2–113.5° C. |
| 5 | $CH_3$ | $CH_3$ | Cl | F | Cl | $OC_3H_7$-i | m.p. 72.0–73.5° C. |
| 6 | $CH_3$ | $CH_3$ | Cl | F | Cl | $OCH_2C\equiv CH$ | m.p. 129.5–131.0° C. |
| 7 | $CHF_2$ | H | Cl | F | Cl | $OC_3H_7$-i | $n^D$ 1.5396 (25.0° C.) |
| 8 | $CHF_2$ | H | Cl | F | Cl | $OCH_2C\equiv CH$ | m.p. 89.1–90.3° C. |
| 9 | $CHF_2$ | H | Cl | F | Cl | $OCH_2COOCH_3$ | m.p. 75.0–77.6° C. |
| 10 | $CHF_2$ | H | Cl | F | Cl | $OCHCOOC_2H_5$<br>$\|$<br>$CH_3$ | $n^D$ 1.5300 (24.0° C.) |
| 11 | $CHF_2$ | H | Br | F | Cl | $OC_3H_7$-i | $n^D$ 1.5491 (25.5° C.) |
| 12 | $CHF_2$ | $CH_3$ | H | F | Cl | $OCH_3$ | m.p. 74.0–75.6° C. |
| 13 | $CHF_2$ | $CH_3$ | H | F | Cl | $OCH_3H_7$-i | m.p. 61.5° C. |
| 14 | $CHF_2$ | $CH_3$ | Cl | Cl | Cl | COOH | m.p. 240.0–207.0° C. |
| 15 | $CHF_2$ | $CH_3$ | Cl | Cl | Cl | $COOCH_3$ | m.p. 100.2–102.0° C. |
| 16 | $CHF_2$ | $CH_3$ | Cl | Cl | Cl | $COOCH_2C\equiv CH$ | m.p. 123.5–124.2° C. |
| 17 | $CHF_2$ | $CH_3$ | Cl | Cl | Cl | $COOCH_2COOCH_3$ | m.p. 91.0–91.9° C. |
| 18 | $CHF_2$ | $CH_3$ | Cl | Cl | Cl | $COOCH_2COOC_2H_5$ | m.p. 84.5–85.5° C |
| 19 | $CHF_2$ | $CH_3$ | Cl | Cl | Cl | $COOCHCOOC_2H_5$<br>$\|$<br>$CH_3$ | $n^D$ 1.5319 (25.0° C.) |
| 20 | $CHF_2$ | $CH_3$ | Cl | Cl | Cl | $COOCH_2COOCH_3$ | $n_D$ 1.5730 (25.0° C.) |
| 21 | $CHF_2$ | $CH_3$ | Cl | F | Cl | OH | m.p. 159.0–163.0° C. |
| 22 | $CHF_2$ | $CH_3$ | Cl | F | Cl | $OCH_3$ | m.p. 122.0–123.0° |
| 23 | $CHF_2$ | $CH_3$ | Cl | F | Cl | $OC_3H_7$-i | $n_D$ 1.5325 (21.0° C.) |
| 24 | $CHF_2$ | $CH_3$ | Cl | F | Cl | $OCHF_2$ | m.p. 67.5–68.0° C. |
| 25 | $CHF_2$ | $CH_3$ | Cl | F | Cl | $OCH_2C\equiv CH$ | m.p. 104.0–104.6° C. |
| 26 | $CHF_2$ | $CH_3$ | Cl | F | Cl | $OC_5H_9$-c | $n^D$ 1.5530 (18.5° C.) |
| 27 | $CHF_2$ | $CH_3$ | Cl | F | Cl | $OCH_2COOCH_3$ | m.p. 88.5–90.0° C. |
| 28 | $CHF_2$ | $CH_3$ | Cl | F | Cl | $OCH_2COOC_2H_5$ | m.p. 117.2–119.1° C. |
| 29 | $CHF_2$ | $CH_3$ | Cl | F | Cl | $OCH_2COOC_3H_7$-i | m.p. 131.5–133.2° C. |
| 30 | $CHF_2$ | $CH_3$ | Cl | F | Cl | $OCH_2COOCH_2C\equiv CH$ | m.p. 84.0–85.1° C. |
| 31 | $CHF_2$ | $CH_3$ | Cl | F | Cl | $OCH_2COOC_2H_4OC_2H_5$ | $n^D$ 1.5301 (24.5° C.) |

TABLE 1-continued

General formula (I')

$$\text{(I')}$$

| No. | R$^1$ | R$^2$ | X | Y$^1$ | Y$^2$ | R$^3$ | Properties |
|---|---|---|---|---|---|---|---|
| 32 | CHF$_2$ | CH$_3$ | Cl | F | Cl | OCHCOOC$_2$H$_5$ <br> \| <br> CH$_3$ | n$^D$ 1.5282 (22.0° C.) |
| 33 | CHF$_2$ | CH$_3$ | Cl | F | Cl | COOCH$_2$CH=CH$_2$ | m.p. 53.5–55.8° C. |
| 34 | CHF$_2$ | CH$_3$ | Cl | F | Cl | COOCHCOOC$_2$H$_5$ <br> \| <br> CH$_3$ | n$^D$ 1.5339 (18.5° C.) |
| 35 | CHF$_2$ | CH$_3$ | Cl | F | Cl | COOCH$_2$COSC$_2$H$_5$ | n$^D$ 1.5616 (18.5° C.) |
| 36 | CHF$_2$ | CH$_3$ | Br | F | Cl | OH | m.p. 170.0–170.5° C. |
| 37 | CHF$_2$ | CH$_3$ | Br | F | Cl | OCH$_3$ | m.p. 128.0–129.2° C. |
| 38 | CHF$_2$ | CH$_3$ | Br | F | Cl | OC$_3$H$_7$-i | n$^D$ 1.5495 (19.0° C.) |
| 39 | CHF$_2$ | CH$_3$ | Br | F | Cl | OCH$_2$C≡CH | m.p. 116.3–117.0° C. |
| 40 | CHF$_2$ | CH$_3$ | Br | F | Cl | OCH$_2$COOCH$_3$ | m.p. 96.6–97.6° C. |
| 41 | CHF$_2$ | CH$_3$ | Br | F | Cl | OCH$_2$COOC$_2$H$_5$ | m.p. 110.0–100.5° C. |
| 42 | CHF$_2$ | CH$_3$ | Br | F | Cl | CH$_2$COO(CH$_2$)$_3$Cl | m.p. 103.0–103.5° C. |
| 43 | CHF$_2$ | CH$_3$ | Br | F | Cl | OCH$_2$COOC$_6$H$_{11}$-c | m.p. 141.0° C. |
| 44 | CHF$_2$ | CH$_3$ | Br | F | Cl | OCH$_2$COOC$_2$H$_4$OD$_2$H$_5$ | m.p. 75.0–76.1° C. |
| 45 | CHF$_2$ | CH$_3$ | Br | F | Cl | OCHCOO(CH$_2$CH$_2$O)$_2$CH$_3$ <br> \| <br> CH$_3$ | n$^D$ 1.5255 (25.5° C.) |
| 46 | CHF$_2$ | CH$_2$Cl | Cl | F | Cl | OC$_3$H$_7$-i | n$^D$ 1.5540 (19.0° C.) |
| 47 | CHF$_2$ | CHCl$_2$ | Cl | F | Cl | OC$_3$H$_7$-i | n$^D$ 1.5541 (19.0° C.) |
| 48 | CF$_2$CHF$_2$ | CH$_3$ | Cl | F | Cl | OC$_3$H$_7$-i | n$^D$ 1.5150 (25.0° C.) |
| 49 | CF$_2$CHF$_2$ | CH$_3$ | Cl | F | Cl | OCH$_2$C≡CH | n$^D$ 1.5298 (25.0° C.) |
| 50 | CF$_2$CHF$_2$ | CH$_3$ | Cl | F | Cl | OCH$_2$COOCH$_3$ | m.p. 115.5–116.3° C. |
| 51 | CF$_2$CHF$_2$ | CH$_3$ | Br | F | Cl | OC$_3$H$_7$-i | n$^D$ 1.5269 (24.0° C.) |
| 52 | CF$_2$CHF$_2$ | CH$_3$ | Br | F | Cl | OCH$_2$COOCH$_3$ | m.p. 125.0–127.0° C. |
| 53 | CF$_2$CHF$_2$ | CH$_3$ | Br | F | Cl | OCH$_2$COOC$_2$H$_5$ | m.p. 128.3–129.6° C. |
| 54 | CF$_2$CHF$_2$ | CH$_3$ | Br | F | Cl | OCH$_2$CON⟨ ⟩ (pyrrolidine) | Paste-like material |
| 55 | CHF$_2$ | CH$_3$ | Cl | Cl | Cl | COOCHCOOCH$_3$ <br> \| <br> CH$_3$ | n$^D$ 1.5432 (25.1° C.) |
| 56 | CHF$_2$ | CH$_3$ | Br | Cl | Cl | COOCHCOOC$_2$H$_5$ <br> \| <br> CH$_3$ | n$^D$ 1.5462 (25.1° C.) |
| 57 | CHF$_2$ | CH$_3$ | Cl | Cl | Cl | COOCHCOO(C$_2$H$_4$O)$_2$CH$_3$ <br> \| <br> CH$_3$ | n$^D$ 1.5462 (25.1° C.) |
| 58 | CHF$_2$ | i-C$_3$H$_7$ | Cl | F | Cl | OCH$_2$C≡CH | m.p. 61.8–62.3° C. |
| 59 | CHF$_2$ | i-C$_3$H$_7$ | Cl | F | Cl | OCHCOOC$_2$H$_5$ <br> \| <br> CH$_3$ | n$^D$ 1.5310 (23.7° C.) |

In Table 1, the expression "-C" is used as a prefix to denote an alicyclic group.

The compounds represented by the general formulas (II), (III), (IX) and (XII), which are each a raw material for producing the present phenylimidazole derivative represented by the general formula (I), can be produced by the following processes.

General formula (II) and general formula (III)

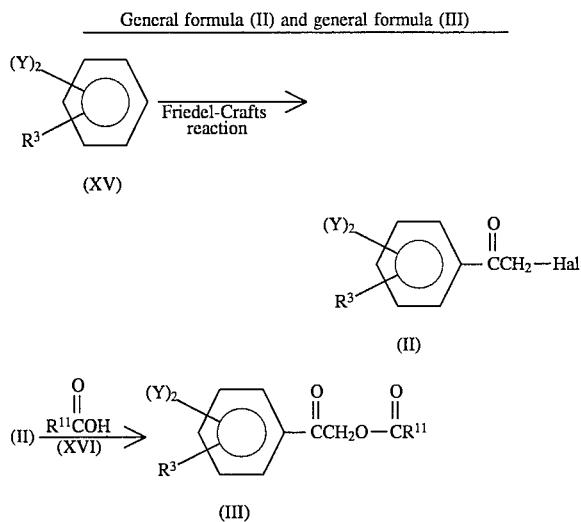

In the above, $R^1$, $R^2$, $R^{11}$ and Hal are the same as defined above.

A compound represented by the general formula (XV) is subjected to a Friedel-Crafts reaction to produce a compound represented by the general formula (II), and the compound is, after isolation or without isolation, reacted with a compound represented by the general formula (XVI) to produce a compound represented by the general formula (III).

General fomula (IX)

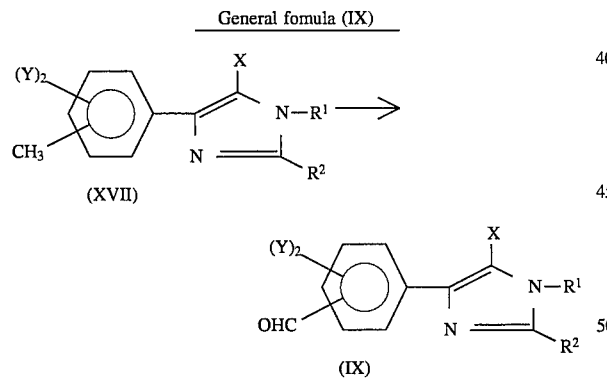

In the above, $R^1$, $R^2$, X and two Ys are the same as defined above.

A compound represented by the general formula (XVII) is produced by a process of the present invention, and the compound (XVII) is converted into a compound represented by the general formula (IX) by the process disclosed in, for example, Japanese Patent Application Kokai (Laid-Open) No. 163063/1991.

The compound represented by the general formula (XII) can be produced by a proces of the present invention.

Typical examples of the present invention are shown below. However, the present invention is not restricted to these examples.

EXAMPLE 1

Production of 4(5)-(4-chloro-2-fluoro-5-isopropoxyphenyl)imidazole (compound No. 2)

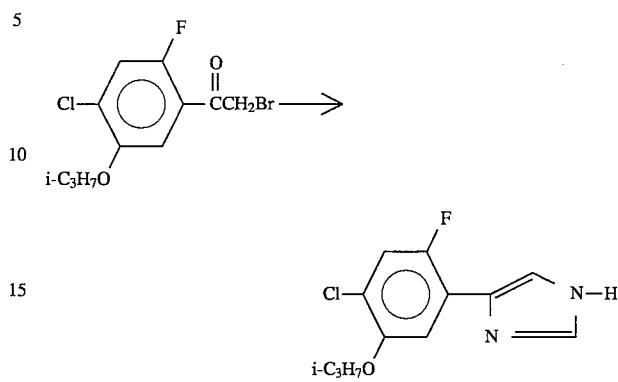

1.25 g (4.04 mM) of 1-bromo-2-(4-chloro-2-fluoro-5-isopropoxyphenyl)-2-ethanone was added to 10 ml of formamide, and a reaction was conducted at 160° C. for 2 hours.

After the completion of the reaction, the reaction mixture was poured into ice water. The resulting mixture was subjected to extraction with ethyl acetate. The ethyl acetate layer was dried over anhydrous magnesium sulfate and subjected to vacuum distillation to remove the solvent. The resulting crude crystals were recrystallized to obtain 0.72 g of an intended product having a melting point of 152.0°–153.0° C., at a yield of 70.0%.

EXAMPLE 2

Production of 4(5)-(4-chloro-2-fluoro-5-methoxyphenyl)-2-methylimidazole (compound No. 1)

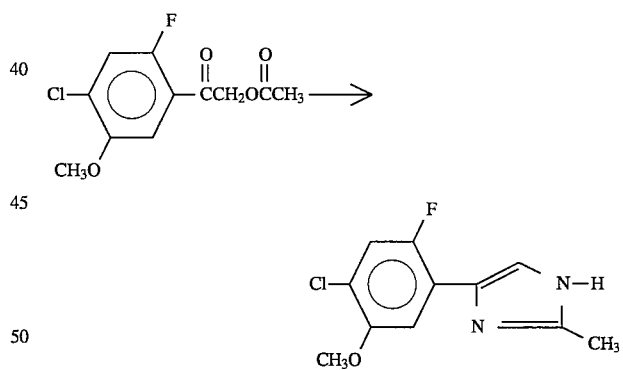

To 100 ml of 28% ammonia water were added, with ice cooling, 9.55 g (195 mM) of a 90% aqueous acetaldehyde solution and 25.96 g (130 mM) of copper acetate monohydrate. Thereto was dropwise added, at room temperature, 16.94 g (65 mM) of 1-acetoxy-2-(4-chloro-2-fluoro-5-methoxyphenyl)-2-ethanone dissolved in 100 ml of dimethylformamide. After the completion of the dropwise addition, a reaction was conducted at room temperature for 3 hours and then at 100° C. for 20 minutes.

After the completion of the reaction, the reaction mixture containing an intended product was poured into ice water. The resulting precipitate was collected by filtration. The precipitate was slowly added to 185 ml of concentrated sulfuric acid, and the mixture was stirred at room temperature for 6 hours. The mixture was then made alkaline with ammonia water and subjected to extraction with ethyl acetate.

The ethyl acetate layer was water-washed, then dried over anhydrous magnesium sulfate, and subjected to vacuum distillation to remove the solvent. The resulting crude crystals were recrystallized to obtain 7.71 g of an intended product having a melting point of 205.0°–207.0° C., at a yield of 49.3%.

EXAMPLE 3

Production of 4-(4-chloro-2-fluoro-5-methoxyphenyl)-1-difluoromethyl-2-methylimidazole (compound No. 12)

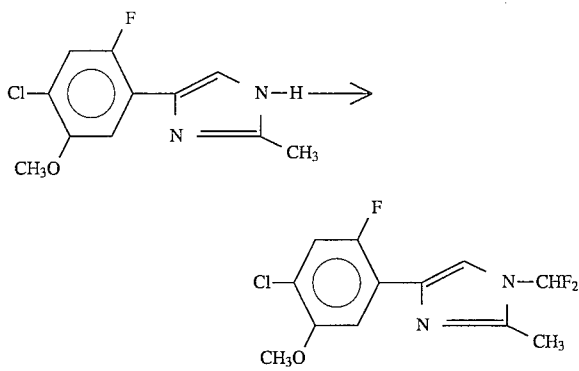

To 50 ml of dimethylformamide were added 2.41 g (10 mM) of 4(5)-(4-chloro-2-fluoro-5-methoxyphenyl)-2-methylimidazole and 1.38 g (20 mM) of potassium carbonate. A reaction was conducted at 90° C. for 4 hours while blowing chlorodifluoromethane (Freon 22 gas) thereinto.

After the completion of the reaction, the reaction mixture containing an intended product was poured into ice water. The resulting mixture was subjected to extraction with ethyl acetate. The ethyl acetate layer was water-washed, dried over anhydrous magnesium sulfate, and subjected to vacuum distillation to remove the solvent to obtain 2.90 g of an oily material.

The oily material was purified by dry column chromatography to obtain 1.86 g of an intended product having a melting point of 74.0°–75.6° C., at a yield of 64.0%.

EXAMPLE 4

Production of 5-chloro-4-(4-chloro-2-fluoro-5-methoxyphenyl)-1-difluoromethyl-2-methylimidazole (compound No. 22)

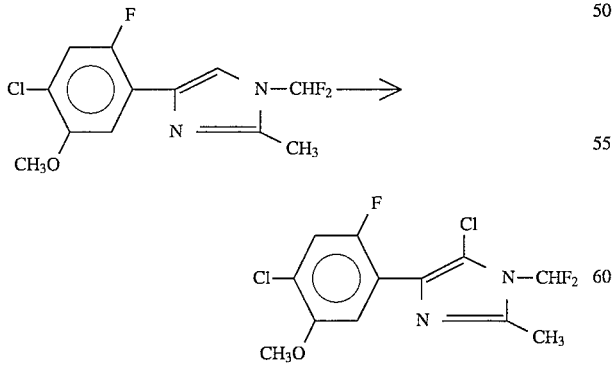

In 50 ml of carbon tetrachloride was dissolved 1.27 g (4.37 mM) of 4-(4-chloro-2-fluoro-5-methoxyphenyl)-1-difluoromethyl-2-methylimidazole. Thereto was added 0.65 g (4.81 mM) of sulfuryl chloride with ice cooling. A reaction was conducted for 3 hours and then at room temperature for 2 hours.

After the completion of the reaction, the reaction mixture containing an intended product was mixed with an aqueous sodium hydrogencarbonate solution and dichloromethane to conduct extraction. The dichloromethane layer was water-washed, dried over anhydrous magnesium sulfate, and subjected to vacuum distillation to remove the solvent. The resulting crude crystals were purified by dry column chromatography to obtian 0.65 g of an intended product having a melting point of 122.0°–123.0° C. at a yield of 45.7%.

EXAMPLE 5

Production of 5-chloro-4-(4-chloro-2-fluoro-5-hydroxyphenyl)-1-difluoromethyl-2-methylimidazole (compound No. 21)

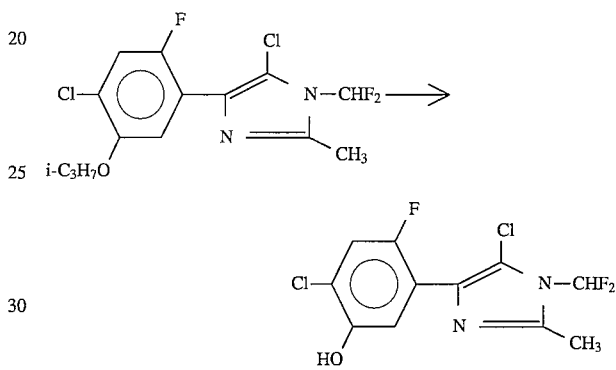

In 10 ml of concentrated sulfuric acid was dissolved 2.10 g (5.95 mM) of 5-chloro-4-(4-chloro-2-fluoro-5-isopropoxyphenyl)-1-difluoromethyl-2-methylimidazole. A reaction was conducted at room temperature for 1 hour.

After the completion of the reaction, the reaction mixture containing an intended product was poured into ice water. The resulting mixture was subjected to extraction with ether. The ether layer was water-washed, dried over anhydrous magnesium sulfate, and subjected to vacuum distillation to remove the solvent to obtain 1.83 g of an intended product having a melting point of 159.0°–163.0° C., at a yield of 98.9%.

EXAMPLE 6

Production of 5-chloro-4-(4-chloro-2-fluoro-5-(2-propynyloxy)phenyl)-1-difluoromethyl-2-methylimidazole (compound No. 25)

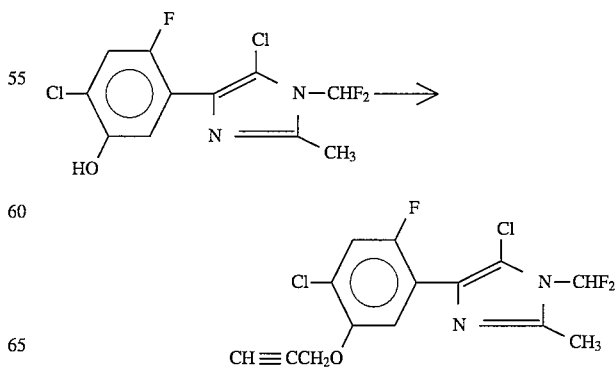

To 20 ml of acetone were added 0.48 g (1.56 mM) of 5-chloro-4-(4-chloro-2-fluoro-5-hydroxyphenyl)-1-difluoromethyl-2-methylimidazole, 0.11 g (0.86 mM) of potassium carbonate and 0.20 g (1.72 mM) of propargyl bromide. A reaction was conducted for 4 hours with refluxing.

After the completion of the reaction, the reaction mixture containing an intended product was poured into ice water. The resulting mixture was subjected to extraction with ethyl acetate. The ethyl acetate layer was water-washed, dried over anhydrous magnesium sulfate, and subjected to vacuum distillation to remove the solvent. The resulting crude crystals were purified by recrystallization to obtain 0.43 g of an intended product having a melting point of 104.0°–104.6° C., at a yield of 78.9%.

EXAMPLE 7

Production of 5-chloro-4-(4-chloro-2-fluoro-5-methoxycarbonylmethoxyphenyl)-1-difluoromethyl-2-methylimidazole (compound No. 27)

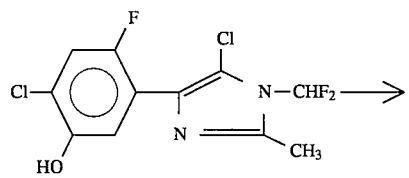

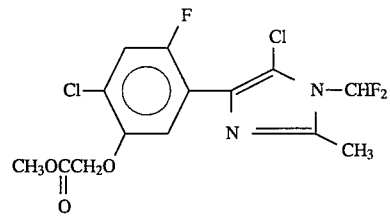

To 30 ml of acetone were added 0.50 g (1.61M) of 5-chloro-4-(4-chloro-2-fluoro-5-hydroxyphenyl)-1-difluoromethyl-2-methylimidazole, 0.13 g (0.97 mM) of potassium carbonate and 0.30 g (1.96 mM) of methyl bromoacetate. A reaction was conducted for 4 hours with refluxing.

After the completion of the reaction, the reaction mixture containing an intended product was poured into ice water. The resulting mixture was subjected to extraction with ethyl acetate. The ethyl acetate layer was water-washed, dried over anhydrous magnesium sulfate, and subjected to vacuum distillation to remove the solvent. The resulting paste-like material was purified by dry column chromatography to obtain 0.52 g of an intended product having a melting point of 88.5°–90.0° C., at a yield of 84.3%.

EXAMPLE 8

Production of 5-(5-chloro-1-difluoromethyl-2-methylimidazol-4-yl)-2,4-dichlorobenzoic acid (compound No. 14)

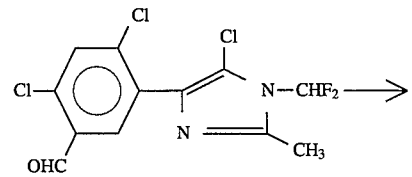

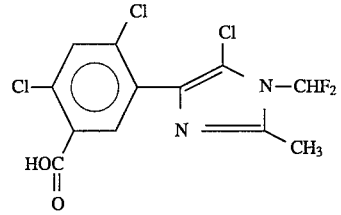

To 10 ml of water was added 0.85 g (2.5 mM) of 5-(5-chloro-1-difluoromethyl-2-methylimidazol-4-yl)-2,4-dichlorobenzaldehyde. The mixture was heated to 80° C. Thereto was dropwise added 0.55 g (3.5 mM) of potassium permanganate dissolved in 11 ml of water, and a reaction was conducted for 1.5 hours.

After the completion of the reaction, the reaction mixture was made alkaline with an aqueous sodium hydroxide solution and then filtered to remove manganese dioxide as a by-product. The filtrate was made acidic with hydrochloric acid and subjected to extraction with ether. The ether layer was water-washed, dried over anhydrous magnesium sulfate, and subjected to vacuum distillation to remove the solvent to obtain 0.54 g of an intended product having a melting point of 204.0°–207.0° C., at a yield of 60.7%.

EXAMPLE 9

Production of methyl 5-(5-chloro-1-difluoromethyl-2-methylimidazol-4-yl)-2,4-dichlorobenzoate (compound No. 15)

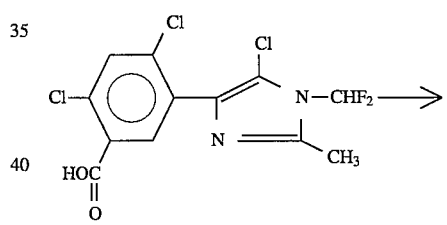

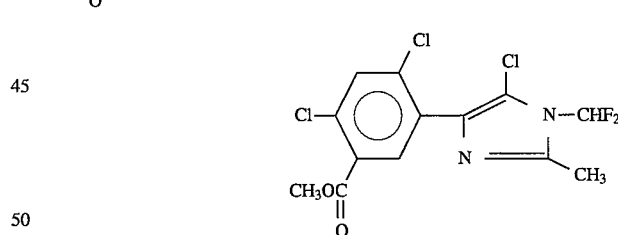

In 30 ml of methanol was dissolved 0.40 g (1.12 mM) of 5-(5-chloro-1-difluoromethyl-2-methylimidazol-4-yl)-2,4-dichlorobenzoic acid. Thereto was added a catalytic amount of concentrated hydrochloric acid, and a reaction was conducted for 14 hours with refluxing.

After the completion of the reaction, the reaction mixture containing an intended product was poured into ice water. The resulting mixture was subjected to extraction with ethyl acetate. The ethyl acetate layer was water-washed, dried over anhydrous magnesium sulfate, and subjected to vacuum distillation to remove the solvent. The resulting paste-like material was purified by dry column chromatography to obtain 0.24 g of an intended product having a melting point of 100.2°–102.0° C., at a yield of 57.7%.

EXAMPLE 10

Production of 2-propynyl 5-(5-chloro-1-difluoromethyl-2-methylimidazol-4-yl)-2,4-dichlorobenzoate (compound No. 16)

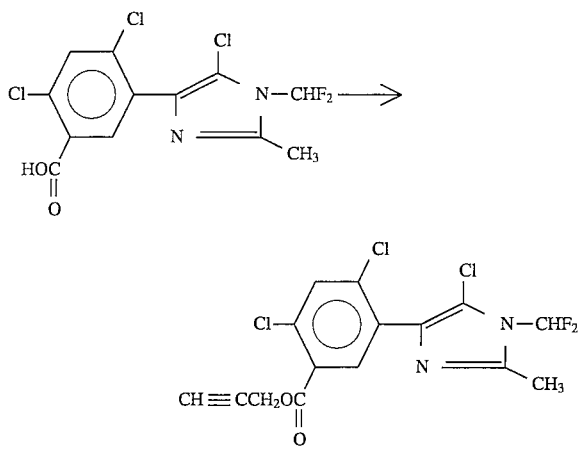

To 10 ml of dimethylformamide were added 0.40 g (1.12 mM) of 5-(5-chloro-1-difluoromethyl-2-methylimidazol-4-yl)-2,4-dichlorobenzoic acid, 0.09 g (0.67 mM) of potassium carbonate and 0.16 g (1.34 mM) of propargyl bromide. A reaction was conducted at 40°–50° C. for 3 hours.

After the completion of the reaction, the reaction mixture containing an intended product was poured into ice water. The resulting mixture was subjected to extraction with ethyl acetate. The ethyl acetate layer was water-washed, dried over anhydrous magnesium sulfate, and subjected to vacuum distillation to remove the solvent. The resulting crude crystals were purified by recrystallization to obtain 0.33 g of an intended product having a melting point of 123.5°–124.2° C., at a yield of 74.5%.

EXAMPLE 11

Production of 5-chloro-4-(4-chloro-2-fluoro-5-isopropoxyphenyl)-2-chloromethyl-1-difluoromethylimidazole (compound No. 46)

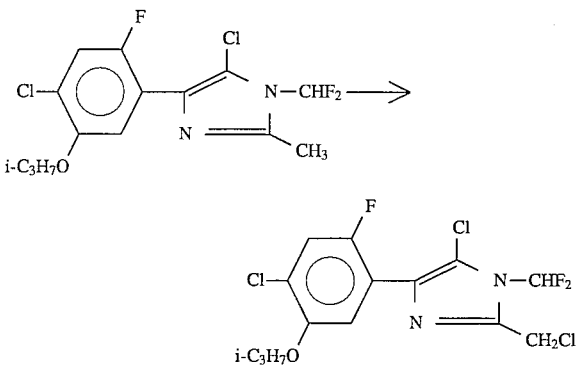

In 50 ml of carbon tetrachloride was dissolved 1.77 g (5 mM) of 5-chloro-4-(4-chloro-2-fluoro-5-isopropoxyphenyl)-1-difluoromethyl-2-methylimidazole. To the solution was dropwise added 1.35 g (10 mM) of sulfuryl chloride. A reaction was conducted for 4 hours with refluxing.

After the completion of the reaction, the reaction mixture was mixed with dichloromethane and an aqueous sodium hydrogencarbonate solution. The organic layer was separated, water-washed, dried over anhydrous magnesium sulfate, and subjected to vacuum distillation to remove the solvent. The resulting paste-like material was purified by dry column chromatography to obtain 1.07 g of an intended product having and of 1.5540 (19° C.), at a yield of 55.2%.

The herbicide comprising, as an active ingredient, the present phenylimidazole derivative represented by the general formula (I) is useful for controlling annual and perennial weeds which grow in paddy fields, upland fields, orchards, swamps, etc., such as barnyard grass (*Echinochloa crusgalli Beauv.*, an annual gramineous grass which is a strongly injurious weed of paddy fields), umbrella plant (*Cyperus difformis L.*, an annual cyperaceous grass which is an injurious weed of paddy fields), slender spikerush (*Eleocharis acicularis Roem.* et Schult, a perennial cyperaceous grass which is a typical injurious weed of paddy fields and which grows also in swamps and waterways), arrowhead (*Sagittaria pygmaea Mig.*, an injurious perennial weed of Alismataceae family which grows in paddy fields, swamps and ditches), bulrush (*Scirpus juncoides Roxb.* var. hotarui ohwi, a perennial cyperaceous weed which grows in paddy fields, swamps and ditches), wild oats (*Avena fatua L.*, a biennial gramineous grass which grows in plains, waste lands and upland fields), mugwort (*Artemisia princeps Pamp.*, a perennial composite grass which grows in cultivated and uncultivated fields and mountains), large crabgrass (*Digitaria adscendcus Henr.*, an annual gramineous grass which is a typical strongly injurious weed of upland fields and orchards), Gishigishi or Japanese dock (*Rumex japonicus Houtt.*, a perennial polygonaceous weed which grows in upland fileds and roadsides), umbrella sedge (*Cyperus iria L.*, an annual cyperaceous weed), redroot pigweed (*Amaranthus varidis L.*, an annual weed of Amaranthaceae family which grows in vacant lands, roadsides and upland fields), cocklebur (*Xanthium strumarium L.*, an injurious annual composite weed which grows in upland fields), velvetleaf (*Abutlion theophrasti L.*, an injurious annual weed of Malvaceae family which grows in upland fields), purple thornapple (*Dutura tatula L.*, an annual injurious weed of Convolvulaceae family which grows in upland fields), bird's eye speedwell (*Veronica persica Poir.*, an injurious biennial weed of Scrophulariaceae family which grows in upland fields) and cleavers (*Galium aparine L.*, an injurious annual weed of Rubiaceae family which grows in upland fields and orchards).

Since the herbicide comprising, as an active ingredient, the present phenylimidazole derivative represented by the general formula (I) exhibits an excellent controlling effect on weeds before or after emergence, the characteristic physiological activities of the herbicide can be effectively manifested by treating fields with the herbicide before planting useful plants therein, or after planting useful plants therein (including the case in which useful plants are already planted as in orchards) but during the period from the initial stage of emergence of weeds to their growth stage.

However, the application of the present herbicide is not restricted only to the modes mentioned above. The present herbicide can be applied to control not only weeds which grow in paddy fields but also weeds which grow in other places such as upland fields, temporarily non-cultivated paddy fields and upland fields, ridges between paddy fields, agricultural pathways, waterways, lands constructed for pasture, graveyards, roads, playgrounds, unoccupied areas around buildings, developed lands, railways, forests and the like.

The treatment of target fields with the present herbicide is most effective in economy when the treatment is made by the initial stage of emergence of weeds. However, the treatment is not restricted thereto and can be carried out even during the growth stage of weeds.

For applying the present phenylimidazole derivative represented by the general formula (I), as a herbicide, the derivative is generally made into a form convenient to use, according to the procedure conventionally employed for preparing agricultural chemicals.

That is, the present phenylimidazole derivative of the general formula (I) is mixed with an appropriate inert carrier and, as necessary, further with an adjuvant, in an appropriate ratio, and the mixture is made into a desired form of preparation, such as suspension, emulsifiable concentrate, solution, wettable powder, granules, dust, tablets and the like, through dissolution, dispersion, suspension, mixing, impregnation, adsorption or adhesion.

The inert carrier usable in the present invention may be a solid or a liquid. Materials usable as the solid carrier include, for example, soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite and acid clay), talcs (e.g. talc and pyrophyllite), silica powders or flakes [e.g. diatomaceous earth, silica sand, mica and white carbon (i.e. highly dispersed silicic acid, also called finely divided hydrated silica or hydrated silicic acid)], activated carbon, powdered sulfur, powdered pumice, calcined diatomaceous earth, ground brick, fly ash, sand, calcium carbonate powder, calcium phosphate powder, other inorganic mineral powders, chemical fertilizers (e.g. ammonium sulfate, ammonium phosphate, ammonium nitrate, urea and ammonium chloride) and compost. These materials can be used alone or in combination of two or more.

The liquid carrier is selected not only from liquids having solvency by themselves but also from liquids having no solvency but capable of dispersing the active ingredient contained in the herbicide, with the aid of adjuvant(s). Typical examples of the liquid carrier, which can be used alone or in combination of two or more, are water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. diethyl ether, dioxane, Cellosolve, diisopropyl ether and tetrahydrofuran), aliphatic hydrocarbons (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

As the adjuvant, there can be mentioned the following typical adjuvants. They are used according to respective purposes. They may be used alone or in combination of two or more, or may not be used at all.

For the purpose of emulsifying, dispersing, solubilizing and/or wetting the active ingredient compound, there are used surface active agents, for example, polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of imparting stable dispersion, tackiness and/or bonding property to the active ingredient compound, there may be used adjuvants such as casein, gelatin, starch, methyl cellulose, carboxymethyl cellulose, gum arabic, polyvinyl alcohol, turpentine, bran oil, bentonite and ligninsulfonates.

For the purpose of improving the flow properties of solid herbicidal composition, there may be used adjuvants such as waxes, stearates and alkyl phosphates.

Adjuvants such as naphthalenesulfonic acid condensation products and polyphosphates may be used as peptizers in dispersible herbicidal composition.

Adjuvants such as silicone oils may be used as deforming agents.

The content of the active ingredient compound may be varied as occasion demands. For example, for the preparation of a powdered or granulated product, the content is 0.01–50% by weight and, also for the preparation of an emulsifiable concentrate or a wettable powder, the content is 0.01–50% by weight as well.

For controlling various weeds or inhibiting their growth, the herbicide comprising, as an active ingredient, the present phenylimidazole derivative of the general formula (I) is applied as such or after being appropriately diluted with or suspended in water or other medium, in an amount effective for controlling weeds or inhibiting their growth, to the foliage and stalks of the weeds or to soil in the area where the emergence or growth of the weeds is undesirable.

The amount of the herbicide comprising, as an active ingredient, the present phenylimidazole derivative of the genral formula (I) used varies depending upon various factors, for example, the purpose of application, the kinds of target weeds, the emergence or growth states of crops, the emergence tendency of weeds, weather, environmental conditions, the form of the herbicide used, the mode of application, the type or state of application site and the time of application. However, the amount is selected appropriately according to the purpose from the range of 0.01 g to 10 kg in terms of the amount of active ingredient compound per hectare.

The herbicide containing, as an active ingredient, the present phenylimidazole derivative of the genral formula (I) can be applied jointly with other herbicides for the purpose of expanding both the spectrum of controllable weeds and the period of time when effective application is possible or for the purpose of reducing the dosage.

Typical formulation examples and test examples of the present herbicide are shown hereinafter. However, the present invention is not restricted to these examples.

In the formulation examples, parts are by weight.

Formulation Example 1

| | |
|---|---|
| Present compound | 50 parts |
| Xylene | 40 parts |
| Mixture of polyoxyethylene nonylphenyl ether and calcium alkylbenzenesulfonate | 10 parts |

The above materials are uniformly mixed to obtain an emulsifiable concentrate.

Formulation Example 2

| | |
|---|---|
| Present compound | 3 parts |
| Clay powder | 82 parts |
| Diatomaceous earth powder | 15 parts |

The above materials are ground and mixed uniformly to obtain a dust.

Formulation Example 3

| Present compound | 5 parts |
| --- | --- |
| Mixed powder of bentonite and clay | 90 parts |
| Calcium ligninsulfonate | 5 parts |

The above materials are uniformly mixed; the mixture is kneaded with an appropriate amount of water; the kneaded product is granulated and dried to obtain granules.

Formulation Example 4

| Present compound | 20 parts |
| --- | --- |
| Kaolin and highly dispersed synthetic silicic acid | 75 parts |
| Mixture of polyoxyethylene nonylphenyl ether and calcium alkylbenzenesulfonate | 5 parts |

The above materials are ground and mixed uniformly to obtain a wettable powder.

Test Example 1

Herbicidal effect on paddy field weeds of post-emergence stage

Pots (1/10,000—are) were filled with soil to simulate a paddy field and then planted with seeds of barnyard grass (*Echinochloa crus-galli Beauv.*) and bulrush (*Scirpus juncoides Roxb.* var. hotarui ohwi) and with tubers of flat sedge (*Cyperus serotinus Rottb.*) and arrowhead (*Sagittaria pygmaea Mig.*) (all of these weeds are injurious weeds which grow in paddy fields). The seeds and tubers were grown so as to each produce one-year leaf.

Then, each pot was treated with a herbicide containing, as the active ingredient, one of the present compounds shown in Table 1.

After 21 days from the treatment, the herbicidal effect was examined and, by comparing with the result of an untreated pot, the weed control (%) of the herbicide used was calculated. Using this weed control, the herbicidal activity of the herbicide used was rated according to the following criterion.

Simultaneously, the phytotoxicity to rice by each herbicide was also examined and rated according to the following criterion.

Criterion for rating herbicidal activity

| Degree of herbicidal activity | Weed control (%) |
| --- | --- |
| 5 | 95 or below |
| 4 | 70 to less than 95 |
| 3 | 50 to less than 70 |
| 2 | 30 to less than 50 |
| 1 | 10 to less than 30 |
| 0 | Less than 10 |

Criterion for rating phytotoxicity

H: Phytotoxicity is high (including withering).
M: Phytotoxicity is medium.
L: Phytotoxicity is low.
N: Phytotoxicity is none.

The results are shown in Table 2.

TABLE 2

| Compound No. | Dosage g/ha | Phytotoxicity to rice | Herbicidal activity | | | |
| --- | --- | --- | --- | --- | --- | --- |
| | | | EC | SJ | CS | SP |
| 5 | 800 | L | 1 | 0 | 5 | 3 |
| 6 | 800 | N | 5 | 3 | 5 | 0 |
| 7 | 800 | N | 4 | 1 | 3 | 0 |
| 8 | 800 | L | 5 | 4 | 5 | 4 |
| 9 | 800 | L | 5 | 4 | 4 | 5 |
| 11 | 800 | N | 4 | 2 | 5 | 1 |
| 14 | 5000 | M | 5 | 5 | 5 | 5 |
| 15 | 5000 | L | 5 | 3 | 0 | 5 |
| 16 | 5000 | M | 5 | 5 | 1 | 5 |
| 17 | 5000 | M | 5 | 4 | 1 | 5 |
| 18 | 5000 | M | 5 | 5 | 5 | 5 |
| 19 | 5000 | M | 5 | 4 | 0 | 5 |
| 20 | 5000 | L | 5 | 4 | 0 | 5 |
| 22 | 5000 | L | 5 | 5 | 5 | 5 |
| 23 | 5000 | L | 5 | 4 | 5 | 2 |
| 24 | 5000 | L | 5 | 4 | 5 | 2 |
| 25 | 5000 | M | 5 | 5 | 5 | 5 |
| 27 | 800 | N | 2 | 5 | 5 | 5 |
| 28 | 800 | N | 3 | 5 | 5 | 5 |
| 29 | 800 | N | 2 | 5 | 5 | 5 |
| 30 | 800 | N | 2 | 5 | 5 | 5 |
| 31 | 800 | L | 0 | 5 | 5 | 5 |
| 32 | 800 | L | 5 | 5 | 5 | 5 |
| 33 | 800 | L | 5 | 4 | 2 | 5 |
| 34 | 800 | L | 5 | 5 | 3 | 5 |
| 35 | 800 | L | 5 | 5 | 5 | 5 |
| 36 | 800 | N | 3 | 5 | 5 | 5 |
| 38 | 800 | N | 5 | 3 | 5 | 5 |
| 39 | 800 | L | 5 | 4 | 5 | 0 |
| 40 | 5000 | N | 4 | 5 | 5 | 5 |
| 41 | 800 | L | 4 | 5 | 5 | 5 |
| 42 | 800 | L | 0 | 5 | 5 | 5 |
| 43 | 800 | N | 0 | 3 | 3 | 5 |
| 44 | 800 | N | 1 | 5 | 5 | 5 |
| 45 | 800 | L | 5 | 5 | 5 | 5 |
| 47 | 800 | N | 1 | 0 | 0 | 5 |
| 48 | 800 | N | 4 | 1 | 5 | 0 |
| 49 | 800 | L | 5 | 2 | 5 | 0 |
| 50 | 800 | L | 5 | 5 | 5 | 5 |
| 54 | 800 | N | 4 | 0 | 5 | 0 |
| 55 | 800 | M | 5 | 5 | 1 | 5 |
| 56 | 800 | M | 4 | 4 | 1 | 5 |
| 57 | 800 | M | 3 | 4 | 1 | 5 |
| 58 | 1000 | N | 5 | 0 | 0 | 2 |
| 59 | 1000 | N | 5 | 0 | 0 | 2 |

Test Example 2

Herbicidal effect on upland field weeds of pre-emergence stage

Polyethylene vats of 10 cm×20 cm×5 cm (depth) were filled with soil and seeded with wild oats (*Avena fatua L.*), barnyard grass (*Echinochloa crus-galli Beauv.*), velvetleaf (*Abutilon theophrasti L.*), cocklebur (*Xanthium strumarium L.*), cleavers (*Galium aparine L echinospermon*) and bird's eye speedwell (*Veronica persica L.*) (these are injurious weeds of upland fields) and also with soybean and wheat both as crops of upland fields. Then, the seeds were covered with soil.

Each vat was treated with a herbicide containing, as the active ingredient, one of the present compounds shown in Table 1, by spraying.

After 14 days from the treatment, the herbicidal effect of the herbicide was examined, and the weed control (%) was calculated and the herbicidal activity was rated, both in the same manners as in Test Example 1.

Simultaneously, the phytotoxicity to soybean and wheat by each herbicide was also examined and rated in the same manner as in Test Example 1.

The results are shown in Table 3.

TABLE 3

| Compound No. | Dosage g/ha | Phytotoxicity | | Herbicidal activity | | | | | |
|---|---|---|---|---|---|---|---|---|---|
| | | Wheat | Soybean | AF | EC | AT | XS | GA | VP |
| 7 | 800 | N | N | 0 | 2 | 2 | 0 | 0 | 5 |
| 8 | 800 | N | N | 2 | 5 | 5 | 2 | 1 | 5 |
| 9 | 800 | N | N | 0 | 2 | 2 | 0 | 0 | 5 |
| 10 | 800 | L | N | 2 | 4 | 5 | 0 | 0 | 5 |
| 11 | 800 | N | N | 1 | 3 | 5 | 0 | 2 | 5 |
| 12 | 5000 | N | N | 1 | 4 | 0 | 0 | 0 | 2 |
| 14 | 5000 | L | L | 2 | 5 | 5 | 5 | 5 | 5 |
| 15 | 800 | N | N | 0 | 2 | 5 | 0 | 0 | 3 |
| 16 | 800 | N | N | 0 | 2 | 4 | 0 | 3 | 5 |
| 17 | 800 | N | N | 0 | 2 | 5 | 0 | 2 | 5 |
| 18 | 5000 | N | N | 0 | 5 | 5 | 5 | 5 | 5 |
| 19 | 800 | N | N | 1 | 4 | 4 | 0 | 0 | 5 |
| 20 | 800 | N | N | 1 | 2 | 5 | 0 | 5 | 5 |
| 21 | 800 | N | N | 0 | 2 | 0 | 0 | 5 | 5 |
| 22 | 5000 | M | N | 5 | 5 | 5 | 4 | 4 | 5 |
| 23 | 5000 | M | L | 5 | 5 | 5 | 2 | 5 | 5 |
| 24 | 5000 | H | L | 5 | 5 | 5 | 4 | 5 | 5 |
| 25 | 5000 | H | N | 5 | 5 | 5 | 5 | 5 | 5 |
| 26 | 800 | N | N | 2 | 5 | 2 | 0 | 0 | 5 |
| 27 | 800 | N | N | 0 | 2 | 5 | 5 | 5 | 5 |
| 28 | 800 | N | N | 0 | 1 | 2 | 0 | 4 | 5 |
| 29 | 800 | N | N | 0 | 2 | 5 | 0 | 4 | 5 |
| 30 | 800 | N | N | 0 | 2 | 5 | 0 | 4 | 5 |
| 32 | 800 | N | N | 0 | 4 | 5 | 3 | 5 | 5 |
| 33 | 800 | N | N | 3 | 4 | 5 | 0 | 2 | 5 |
| 34 | 800 | N | N | 0 | 4 | 5 | 0 | 5 | 5 |
| 35 | 800 | N | N | 2 | 3 | 4 | 0 | 5 | 5 |
| 37 | 800 | N | N | 0 | 5 | 3 | 0 | 0 | 5 |
| 38 | 800 | N | N | 4 | 5 | 4 | 0 | 2 | 5 |
| 39 | 800 | L | N | 2 | 5 | 5 | 4 | 0 | 5 |
| 40 | 800 | N | N | 0 | 3 | 5 | 0 | 5 | 5 |
| 42 | 800 | N | N | 0 | 0 | 2 | 0 | 0 | 5 |
| 43 | 800 | N | L | 0 | 3 | 5 | 2 | 0 | 5 |
| 45 | 800 | N | N | 0 | 2 | 5 | 0 | 0 | 5 |
| 48 | 800 | N | N | 2 | 5 | 5 | 2 | 0 | 5 |
| 49 | 800 | N | N | 4 | 5 | 5 | 4 | 0 | 5 |
| 50 | 800 | N | N | 2 | 5 | 2 | 2 | 0 | 5 |
| 51 | 800 | N | N | 3 | 5 | 5 | 0 | 0 | 5 |
| 52 | 800 | L | N | 2 | 3 | 5 | 0 | 0 | 5 |
| 53 | 800 | L | N | 2 | 3 | 5 | 0 | 0 | 5 |
| 54 | 800 | N | L | 0 | 5 | 5 | 4 | 5 | 5 |
| 55 | 800 | N | N | 0 | 3 | 5 | 0 | 5 | 5 |
| 56 | 800 | N | N | 0 | 3 | 4 | 0 | 5 | 5 |
| 57 | 800 | N | N | 0 | 3 | 3 | 0 | 2 | 5 |
| 58 | 1000 | N | N | 0 | 1 | 0 | 0 | 0 | 5 |
| 59 | 1000 | N | N | 0 | 1 | 3 | 0 | 0 | 5 |

Test Example 3

Herbicidal effect on upland field weeds of post-emergence stage

Polyethylene vats of 10 cm×20 cm×5 cm (depth) were filled with soil and seeded with various injurious weeds of upland fields shown below and also with soybean and wheat both as crops of upland fields. Then, the seeds were covered with soil and grown to the following leaf stages.

Each vat was treated with a herbicide containing, as the active ingredient, one of the present compounds shown in Table 1, by spraying.

After 14 days from the treatment, the herbicidal effect of the herbicide was examined, and the weed control (%) was calculated and the herbicidal activity was rated, both in the same manners as in Test Example 1.

Simultaneously, the phytotoxicity to soybean and wheat by each herbicide was also examined and rated in the same manner as in Test Example 1.

Weeds tested and their leaf stages, and leaf stages of soybean and wheat

| Weed or crop | Leaf stage |
|---|---|
| Wild oats (AF) | 2 |
| Barnyard grass (EC) | 2 |
| Velvetleaf (AT) | 1 |
| Cocklebur (XS) | 1 |
| Cleavers (GA) | 2 |
| Bird's eye speedwell (VP) | 1 |
| Wheat | 2 |
| Soybean | 1 |

The results are shown in Table 4.

TABLE 4

| Compound No. | Dosage g/ha | Phytotoxicity Wheat | Phytotoxicity Soybean | Herbicidal activity AF | EC | AT | XS | GA | VP |
|---|---|---|---|---|---|---|---|---|---|
| 1 | 5000 | N | N | 2 | 2 | 1 | 0 | 2 | 0 |
| 3 | 5000 | L | L | 2 | 2 | 2 | 0 | 2 | 0 |
| 5 | 800 | L | M | 3 | 2 | 5 | 2 | 4 | 5 |
| 6 | 800 | L | L | 2 | 2 | 5 | 2 | 5 | 5 |
| 7 | 800 | L | M | 2 | 2 | 5 | 3 | 5 | 5 |
| 8 | 800 | L | M | 3 | 3 | 5 | 2 | 5 | 5 |
| 9 | 800 | M | H | 3 | 4 | 5 | 5 | 5 | 5 |
| 10 | 800 | H | H | 5 | 5 | 5 | 5 | 5 | 5 |
| 11 | 800 | L | L | 2 | 2 | 5 | 2 | 4 | 4 |
| 12 | 5000 | L | M | 3 | 3 | 4 | 2 | 3 | 4 |
| 13 | 5000 | L | L | 3 | 3 | 3 | 2 | 3 | 2 |
| 14 | 5000 | M | H | 3 | 5 | 5 | 5 | 5 | 5 |
| 15 | 800 | L | M | 3 | 5 | 5 | 5 | 4 | 4 |
| 16 | 800 | L | H | 2 | 2 | 5 | 4 | 4 | 5 |
| 17 | 800 | N | H | 2 | 4 | 5 | 5 | 5 | 5 |
| 18 | 5000 | M | H | 5 | 5 | 5 | 5 | 5 | 5 |
| 19 | 800 | M | H | 5 | 5 | 5 | 5 | 5 | 5 |
| 20 | 800 | L | H | 4 | 4 | 5 | 5 | 5 | 5 |
| 21 | 800 | L | M | 3 | 5 | 5 | 4 | 3 | 3 |
| 22 | 5000 | H | H | 5 | 5 | 5 | 5 | 5 | 5 |
| 23 | 5000 | M | H | 5 | 5 | 5 | 5 | 5 | 5 |
| 24 | 5000 | M | H | 5 | 5 | 5 | 5 | 5 | 5 |
| 25 | 5000 | H | H | 5 | 5 | 5 | 5 | 5 | 5 |
| 26 | 800 | L | H | 4 | 4 | 5 | 5 | 5 | 5 |
| 27 | 800 | L | M | 2 | 2 | 5 | 5 | 4 | 4 |
| 28 | 800 | N | M | 1 | 3 | 5 | 5 | 5 | 5 |
| 29 | 800 | N | M | 1 | 2 | 5 | 4 | 4 | 5 |
| 30 | 800 | N | H | 1 | 2 | 5 | 5 | 4 | 5 |
| 31 | 800 | L | H | 2 | 2 | 5 | 5 | 4 | 5 |
| 32 | 800 | L | H | 2 | 5 | 5 | 5 | 3 | 5 |
| 33 | 800 | L | H | 4 | 5 | 5 | 5 | 5 | 5 |
| 34 | 800 | L | H | 4 | 5 | 5 | 5 | 5 | 5 |
| 35 | 800 | N | H | 1 | 5 | 5 | 5 | 5 | 5 |
| 36 | 800 | M | H | 3 | 2 | 5 | 4 | 5 | 4 |
| 37 | 800 | M | H | 5 | 4 | 5 | 2 | 5 | 5 |
| 38 | 800 | L | H | 3 | 4 | 5 | 5 | 4 | 5 |
| 39 | 800 | H | H | 5 | 5 | 5 | 5 | 5 | 5 |
| 40 | 800 | N | H | 2 | 2 | 5 | 5 | 5 | 5 |
| 41 | 800 | N | L | 2 | 2 | 5 | 5 | 5 | 5 |
| 42 | 800 | N | N | 1 | 2 | 5 | 5 | 3 | 3 |
| 43 | 800 | L | H | 2 | 3 | 5 | 5 | 5 | 5 |
| 44 | 800 | L | H | 1 | 2 | 5 | 5 | 5 | 5 |
| 45 | 800 | L | L | 2 | 3 | 5 | 5 | 4 | 5 |
| 46 | 800 | N | M | 2 | 2 | 5 | 1 | 3 | 2 |
| 47 | 800 | N | M | 2 | 2 | 4 | 2 | 4 | 5 |
| 48 | 800 | L | M | 4 | 3 | 5 | 3 | 4 | 5 |
| 49 | 800 | M | H | 5 | 5 | 5 | 5 | 5 | 5 |
| 50 | 800 | H | H | 4 | 4 | 5 | 5 | 5 | 5 |
| 51 | 800 | M | H | 5 | 4 | 5 | 5 | 4 | 5 |
| 52 | 800 | M | H | 5 | 4 | 5 | 5 | 5 | 5 |
| 53 | 800 | M | H | 3 | 3 | 5 | 4 | 4 | 5 |
| 54 | 800 | L | H | 2 | 3 | 5 | 5 | 4 | 5 |
| 55 | 800 | H | H | 4 | 5 | 5 | 5 | 5 | 5 |
| 56 | 800 | M | H | 4 | 5 | 5 | 5 | 5 | 5 |
| 57 | 800 | H | H | 4 | 5 | 5 | 5 | 5 | 5 |
| 58 | 1000 | M | H | 3 | 2 | 5 | 4 | 4 | 5 |
| 59 | 1000 | N | H | 1 | 2 | 5 | 5 | 4 | 5 |

What is claimed is:

1. A phenylimidazole derivative represented by the following formula (I)

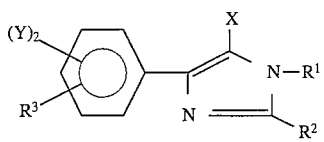

wherein $R^1$ is a hydrogen atom or difluoromethyl group; $R^2$ is a methyl group; X is a hydrogen atom; two Ys are 2-fluoro atom and 4-chloro atom; and $R^3$ is a group represented by the following formula $$-A'-R^4$$

wherein A' is an oxygen atom; $R^4$ is a hydrogen atom or a group represented by the following formula $$-CH_2COOR^6$$

wherein $R^6$ is an alkyl group of 1–5 carbon atoms.

2. A herbicidal composition comprising a herbicidal effective amount of an active ingredient, a phenylimidazole derivative represented by the following formula (I)

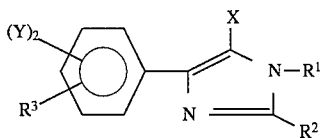

wherein $R^1$ is a hydrogen atom or difluoromethyl group; $R^2$ is a methyl group; X is a hydrogen atom; two Ys are 2-fluoro atom and 4-chloro atom; and $R^3$ is a group represented by the following formula

—A'—$R^4$ wherein A' is an oxygen atom; $R^4$ is a hydrogen atom or a group represented by the following formula

—CH$_2$COO$R^6$ wherein $R^6$ is an alkyl group of 1–5 carbon atoms.

3. A method for controlling weeds, which comprises applying, in order to protect crops from noxious weeds, a herbicidal composition comprising, an effective amount of an active ingredient, a phenylimidazole derivative represented by the following formula (I)

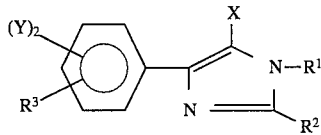

wherein $R^1$ is a hydrogen atom or difluoromethyl group; $R^2$ is a methyl group; X is a hydrogen atom; two Ys are 2-fluoro atom and 4-chloro atom; and $R^3$ is a group represented by the following formula

—A'—$R^4$ wherein A' is an oxygen atom; $R^4$ is a hydrogen atom or a group represented by the following formula

—CH$_2$COO$R^6$ wherein $R^6$ is an alkyl group of 1–5 carbon atoms.

4. A phenylimidazole derivative according to claim 1 which is 5-bromo-4-(4-chloro-2-fluoro-5-ethoxycarbonyl-methoxyphenyl)-1-difluoromethyl-2-methylimidazole.

5. A phenylimidazole derivative according to claim 1 which is 5-bromo-4-(4-chloro-2-fluoro-5-methoxycarbonyl-methoxyphenyl)-1-difluoromethyl-2-methylimidazole.

6. A phenylimidazole derivative according to claim 1 which is 5-bromo-4-(4-chloro-2-fluoro-5-hydroxyphenyl)-1-difluoromethyl-2-methylimidazole.

7. A herbicidal composition according to claim 2 wherein the phenylimidazole derivative is 5-bromo-4-(4-chloro-2-fluoro-5-ethoxycarbonyl-methoxyphenyl)-1-difluoromethyl-2-methylimidazole.

8. A herbicidal composition according to claim 2 wherein the phenylimidazole derivative is 5-bromo-4-(4-chloro-2-fluoro-5-methoxycarbonyl-methoxyphenyl)-1-difluoromethyl-2-methylimidazole.

9. A herbicidal composition according to claim 2 wherein the phenylimidazole derivative is 5-bromo-4-(4-chloro-2-fluoro-5-hydroxyphenyl)-1-difluoromethyl-2-methylimidazole.

10. A method for controlling weeds according to claim 3, wherein the phenylimidazole derivative is 5-bromo-4-(4-chloro-2-fluoro-5-ethoxycarbonyl-methoxyphenyl)-1-difluoromethyl-2-methylimidazole.

11. A method for controlling weeds according to claim 3, wherein the phenylimidazole derivative is 5-bromo-4-(4-chloro-2-fluoro-5-methoxycarbonyl-methoxyphenyl)-1-difluoromethyl-2-methylimidazole.

12. A method for controlling weeds according to claim 3, wherein the phenylimidazole derivative is 5-bromo-4-(4-chloro-2-fluoro-5-hydroxyphenyl)-1-difluoromethyl-2-methylimidazole.

* * * * *